United States Patent [19]
Cantor

[11] Patent Number: 5,994,085
[45] Date of Patent: Nov. 30, 1999

[54] METHODS AND DEVICES FOR DETECTING NON-COMPLEXED PROSTATE SPECIFIC ANTIGEN

[76] Inventor: Thomas L. Cantor, 11149 Shining Light Way, El Cajon, Calif. 92020

[21] Appl. No.: 08/918,839

[22] Filed: Aug. 26, 1997

[51] Int. Cl.$^6$ ............... G01N 33/574; G01N 33/537; G01N 33/541

[52] U.S. Cl. ............... 435/7.1; 435/7.23; 435/7.92; 435/962; 436/174; 436/175; 436/177; 436/178; 436/518; 436/536; 436/538; 436/539; 436/540; 436/541; 436/64; 436/811; 436/813; 436/824; 436/825

[58] Field of Search ............... 435/7.1, 7.23, 435/7.92, 962; 436/174, 175, 177, 178, 518, 536, 538, 539, 540, 541, 64, 811, 813, 824, 825

[56] References Cited

U.S. PATENT DOCUMENTS

| | | | |
|---|---|---|---|
| 4,863,851 | 9/1989 | McEwan et al. | 436/548 |
| 5,501,983 | 3/1996 | Lilja et al. | 436/518 |
| 5,599,677 | 2/1997 | Dowell et al. | 435/7.4 |
| 5,601,988 | 2/1997 | Gordon | 435/7.23 |
| 5,654,161 | 8/1997 | Tewari | 435/7.23 |
| 5,672,480 | 9/1997 | Dowell et al. | 435/7.4 |
| 5,710,007 | 1/1998 | Luderer et al. | 435/7.1 |
| 5,719,032 | 2/1998 | Vielkind | 435/7.23 |
| 5,723,302 | 3/1998 | Diamandis | 435/7.1 |

*Primary Examiner*—Christopher L. Chin
*Attorney, Agent, or Firm*—Brian D. Voyce

[57] ABSTRACT

The present invention relates to novel methods and devices for detecting non-complexed prostate specific antigen (free PSA), which is used in conjunction with total PSA tests to identify patients having either benign prostatic diseases (BPD), such as benign prostatic hyperplasia, prostatitis, or glandular atrophy or prostatic adenocarcinoma (CAP). In a biological sample, one can find not only free PSA, but also prsotate specific antigen (PSA) which has formed a complex with α1-antichymotrypsin (ACT). The present invention removes complexed PSA (PSA-ACT) from a fluid sample, thereby removing any possible interference due to binding of complexed PSA to an allegedly free PSA specific antibody in an immunoassay for free PSA. The method requires contacting a biological fluid sample possibly containing a mixture of complexed PSA and free PSA with a device which specifically binds only complexed PSA, leaving any free PSA unbound, prior to exposing the sample to assay reagents and conditions for detecting free PSA in a specific binding reaction. The device can be a filter having a modified filter media that permits the sample to flow or be pulled through the filter media and into assay reagents. Alternatively, the device can be a removable media that is placed into a sample, allowed to remain long enough to bind any complexed PSA present, and then withdrawn from the sample prior to running a free PSA specific binding assay.

11 Claims, 4 Drawing Sheets

METHODS AND DEVICES FOR DETECTING NON-COMPLEXED PROSTATE SPECIFIC ANTIGEN

TECHNICAL FIELD

The present invention relates to novel methods and devices for detecting non-complexed prostate specific antigen (free PSA), which is used in conjunction with total PSA tests to identify patients having either benign prostatic diseases (BPD), such as benign prostatic hyperplasia, prostatitis, or glandular atrophy or prostatic adenocarcinoma (CAP). In a biological sample, one can find not only free PSA, but also prostate specific antigen (PSA) which has formed a complex with α1-antichymotrypsin (ACT). The present invention removes complexed PSA (PSA-ACT) from a fluid sample, thereby removing any possible interference due to binding of complexed PSA to an allegedly free PSA specific antibody in an immunoassay for free PSA. The method requires contacting a biological fluid sample possibly containing a mixture of complexed PSA and free PSA with a device which specifically binds only complexed PSA, leaving any free PSA unbound, prior to exposing the sample to assay reagents and conditions for detecting free PSA in a specific binding reaction. The device can be a filter having a modified filter media that permits the sample to flow or be pulled through the filter media and into assay reagents. Alternatively, the device can be a removable media that is placed into a sample, allowed to remain long enough to bind any complexed PSA present, and then withdrawn from the sample prior to running a free PSA specific binding assay.

BACKGROUND ART

PSA is recognized as a molecular marker for CAP. Blood or serum based immunoassays measuring the total PSA level have been commercially available for a number of years. However, the detection of total PSA does not necessarily mean that a patient has CAP. In order to distinguish CAP, a total PSA test has to satisfy two elements: a high sensitivity—the ability to detect disease when present, and a high specificity—the ability to detect true negatives and avoid false positives. From clinical experience, total PSA tests have become generally accepted as being predictive of CAP if the total PSA level is greater than 10.0 ng/ml. Total PSA values between 0.0 ng/ml and about 3.9 ng/ml have been considered generally predictive of no disease being present, with a value of about 3.5 ng/ml being used for men under 60 years old and about 2.5 ng/ml being used for men under 50 years old. (See Oesterling, J. E., Cooner, W. H., Jacobsen, S. J., Guess H. A., and Lieber, M. M.: "*Influence of Patient Age on the Serum PSA Concentration and Important Clinical Observations*": Urol. Clin. North Am.; Vol. 20: 671–680, 1993.)

PSA is primarily organ-specific, not cancer specific. Thus, PSA in blood or serum can result not only from CAP, but also from normal or hyperplastic prostate tissues. Historically, a total PSA test cannot reliably distinguish BPD from CAP at less than 10.0 ng/ml. Studies have found that 43% (136/319) of patients with organ-confined CAP have a total PSA value within the normal range of less than 4.0 ng/ml. Moreover, about 25% (148/597) of men with BPD have a total PSA value above 4.0 ng/ml. (See Oesterling, J. E.: "*Prostate Specific Antigen: A Critical Assessment of the Most Useful Tumor Marker for Adenocarcinoma of the Prostate*", J. Urol., Vol: 145: 907–923, 1991.) Standard medical practice is to biopsy patients over 60 years old having total PSA levels of between 4.0 ng/ml and 10.0 ng/ml because about 30% of those patients have CAP. Likewise, patients between 50 years and 60 years old whose total PSA falls between 3.5 ng/ml and 10.0 ng/ml and patients under 50 years old whose total PSA falls between 2.5 ng/ml and 10.0 ng/ml are also biopsied under current medical practice.

One proposed method for detecting CAP is disclosed in U.S. Pat. No. 5,501,983 to Hans Lilja et alia. In general, the Lilja patent discloses using immunoassays to measure free PSA and a complexed form of PSA. Free PSA is a 33 kDa single chain glycoenzyme that is produced by the epithelial cells lining the acini and prostatic ducts of the prostate gland. Complexed PSA refers primarily to a 90 kDa complex of PSA bound to α1-antichymotrypsin (ACT) protein. Free PSA and complexed PSA, and their proportions are applied in the diagnosis of patients with CAP. Throughout, the specification discloses using a combination of a free PSA to total PSA (F/T) proportion and a complexed PSA to total PSA (C/T) proportion for use in diagnosing CAP. No prostate needle biopsy were performed on the patients, and the patients covered a full range of total PSA values. The text provides no guidance as to specifically how one uses these proportions.

A significant advance in diagnosing BPD in a male human patient without requiring a biopsy is disclosed by Luderer, A. A., et alia in "*Measurement of the Proportion of Free to Total Prostate-Specific Antigen Improves Diagnostic Performance of Prostate-Specific Antigen in The Diagnostic Gray Zone of Total Prostate-Specific Antigen*", Urol., Vol. 46: 187–194, 1995. This reflex method eliminates the need for about one-third of those patients to undergo such a biopsy. For those patients in the gray diagnostic zone, the method comprises four steps. First, one measures the total PSA level in the blood or serum of the patient. Second, one measures the free PSA level in the blood or serum of a patient, but only if he has a total PSA level of between about 2.5 ng/ml and about 10.0 ng/ml. If the patient has a total PSA level below 2.5 ng/ml, then he is diagnosed to have BPD. If the patient has a total PSA level above 10.0 ng/ml, then he is presumed to have CAP and must be biopsied. Third, one calculates the proportion of free PSA to total PSA. Fourth and finally, one diagnoses the patient as having BPD if the calculated proportion of free PSA to total PSA is equal to or greater than about 25%.

The removal of an unwanted component from a biological sample is disclosed in U.S. Pat. No. 5,403,745 to James F. Ollington et alia. When assaying for a cholesterol analyte in a targeted lipoprotein class, there can be present in a sample at least one cholesterol-containing interfering substance in another liporotein class. This interfering substance is removed by binding the interfering substance with immobilized antibodies.

DISCLOSURE OF THE INVENTION

The present invention relates to a method for detecting free PSA in a biological sample using an assay that incorporates a specific binding reaction. The present invention removes complexed PSA from a fluid sample, thereby removing any possible interference due to binding of complexed PSA to an allegedly free PSA specific antibody in an immunoassay for free PSA. In particular, the present invention involves either pretreating a fluid sample so as to remove complexed PSA before performing an assay for free PSA or forming an insoluble complex which contains any complexed PSA present in the sample. The pretreating method comprises four steps. First, one contacts a biological fluid sample containing a mixture of complexed PSA and free PSA with a pretreatment device. The pretreatment device has attached to its surfaces an excess of a plurality of at least one specific binding partner which specifically bind only to complexed PSA and not to free PSA, leaving any free PSA unbound. Next, one keeps the fluid sample in contact with the pretreatment device for a time sufficient to bind all complexed PSA to any attached specific binding partners. Thirdly, one removes the fluid sample from the device. The fluid sample is exposed to conventional specific binding assay reagents for detecting free PSA under conditions which permit a measurement of free PSA. Finally, one measures the amount of free PSA present in the fluid sample.

Another aspect of the present invention are devices for pretreating a biological sample that is to be assayed for free PSA. In one embodiment, such a pretreatment device comprises two main elements. The first is a filter that has a modified filter media. The filter is dimensioned and configured so as to permit the fluid sample to flow or be pulled through the filter media and into a vessel containing assay reagents. Suitable filter devices are commercially available. The second element is that the modified filter media has attached to the surface thereof an excess of a plurality of at least one specific binding partner which specifically bind only to complexed PSA and not to free PSA, leaving any free PSA unbound. In an alternative embodiment, the pretreatment device comprises a removable media having attached to the surface thereof an excess of a plurality of at least one specific binding partner which specifically bind only to complexed PSA and not to free PSA, leaving any free PSA unbound. The removable media can be conventional assay type media such as beads, strips. The removable media is dimensioned and configured so as to be placed into and withdrawn from the fluid sample which is placed in a vessel. In yet another alternative embodiment, the pretreatment device comprises a fluid sample vessel having attached to the surface thereof an excess of a plurality of at least one specific binding partner which specifically bind only to complexed PSA and not to free PSA, leaving any free PSA unbound.

The present invention also includes two methods for removing complexed PSA from a sample that do not require any pretreatment device, but instead rely upon forming an insoluble complex that contains all of the complexed PSA present in the sample. The first method comprises seven steps. A biological fluid sample containing a mixture of complexed PSA and free PSA is mixed with an excess of at least one first specific binding partner which specifically binds only to complexed PSA and not to free PSA, leaving any free PSA unbound. The fluid sample is kept in contact with the first specific binding partner for a time sufficient to bind all complexed PSA. An excess of at least one second specific binding partner is added to the sample. This second binding partner specifically binds to the first binding partner when it, in turn, is bound to complexed PSA, thereby forming an insoluble complex containing complexed PSA, the first binding partner and the second binding partner. Neither of these specific binding partners interferes or binds to free PSA. Such antibodies are commercially available from Scantibodies, Inc. of Santee, Calif. For example, a goat anti-α1-antichymotrypsin antibody is used for the first specific binding partner and a rabbit anti-goat antibody is used for the second specific binding partner. The fluid sample is kept in contact with the second specific binding partner for a time and under conditions sufficient to bind all of the complexed PSA which is bound to the first specific binding partner, which are known to those of skill in the art. The insoluble complex is removed from fluid sample by conventional techniques such as filtering, centrifugation, settling, pipetting or the like. With all of the complexed PSA now removed, the fluid sample is exposed to specific binding assay reagents for detecting free PSA under conditions which permit a measurement of free PSA. A variety of reagents and assay formats are known to those of skill in the art. The amount of free PSA present in the fluid sample is measured in accordance with known measuring techniques for the assay.

A second method can be used to remove an insoluble complex containing complexed PSA. A biological fluid sample containing a mixture of complexed PSA and free PSA is contacted with an excess of at least one first specific binding partner which specifically binds only to complexed PSA and not to free PSA, leaving any free PSA unbound. The fluid sample is kept in contact with the first specific binding partner for a time and under conditions sufficient to bind all complexed PSA, as is known by those of skill in the art. An excess of at least one second specific binding partner which specifically binds to the first binding partner is added to the sample. This second binding partner specifically binds to the first binding partner when it, in turn, is bound to complexed PSA, thereby forming an insoluble complex containing the complexed PSA, the first binding partner and the second binding partner. Neither of these specific binding partners interferes or binds to free PSA. Such antibodies are commercially available from Scantibodies, Inc. of Santee, Calif. The fluid sample is kept in contact with the second specific binding partner for a time and under conditions sufficient to bind all of the complexed PSA which is bound to the first specific binding partner, as is known by those of skill in the art. Unlike the previous method, the insoluble complex does not have to be removed from the sample before any free PSA present participates in a specific binding reaction which is used in the conventional assay to measure free PSA. The fluid sample is exposed to specific binding assay reagents for detecting free PSA under conditions which permit free PSA to be bound, and eventually to permit a measurement of free PSA. For example, if free PSA is measured using a sandwich immunoassay, then the sample may be placed in a coated tube having two antibodies. The first antibody is specific for free PSA and is affixed to the tube. The second antibody is specific for another epitope site on the free PSA and contains a signal component that can be measured, such as a radioisotope, an enzyme, a fluorescer, or a luminescent molecule. A sandwich is formed with free PSA in the middle. No complexed PSA from the sample is bound in a sandwich form because it is already bound in the insoluble complex. Prior to measurement of the free PSA, the insoluble complex can be removed by a washing step.

BEST MODES FOR CARRYING OUT THE INVENTION

Free PSA Assay

Figure 1:
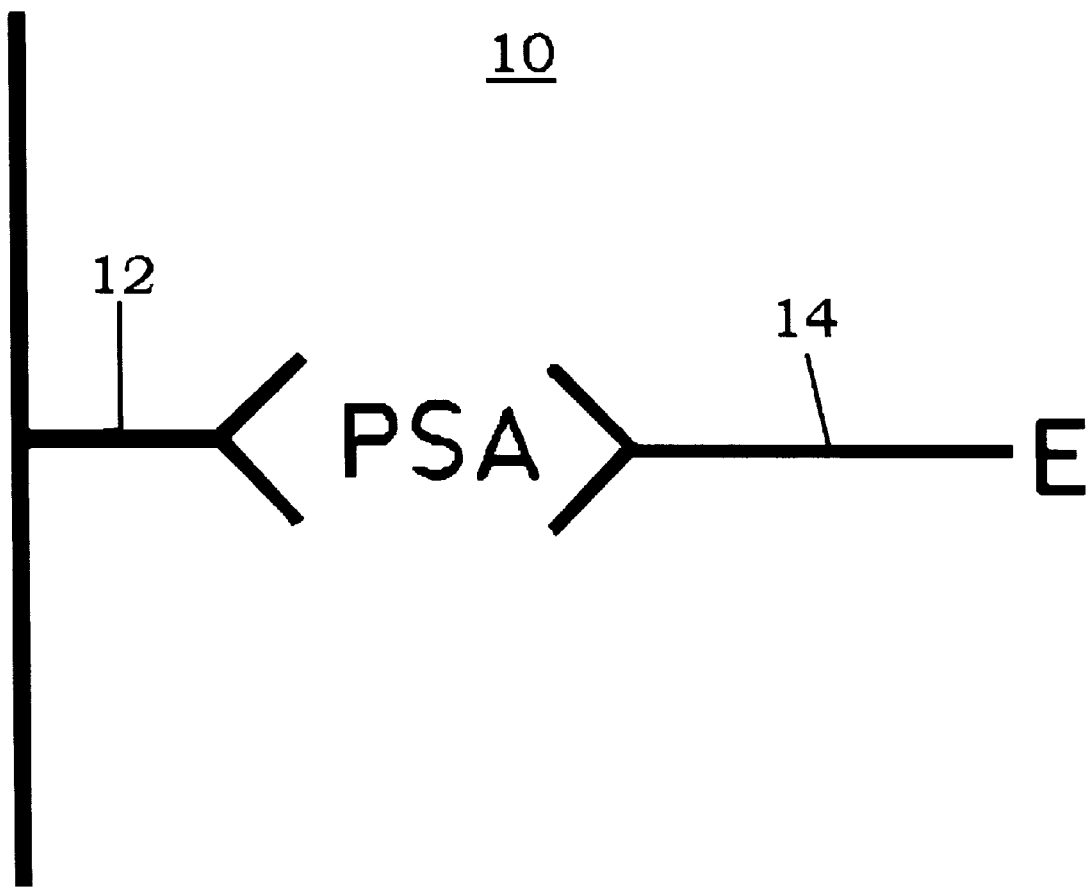
FIG. 1 is a diagrammatic view of an immunoassay for free PSA.

In preferred embodiment described below, the present method comprises an immunoassay, however, any specific binding assay that measures free PSA is suitable for the present methods. The free PSA assay is a sandwich monoclonal/monoclonal immunoassay manufactured by Tosoh Medics, Inc. (Tosoh) of Foster City, Calif. FIG. 1 shows diagrammatically how, in the final configuration, this assay captures free PSA (10) using a capture antibody (12) and an enzyme labeled antibody (14).

Pretreatment Filter Device

Figure 2:
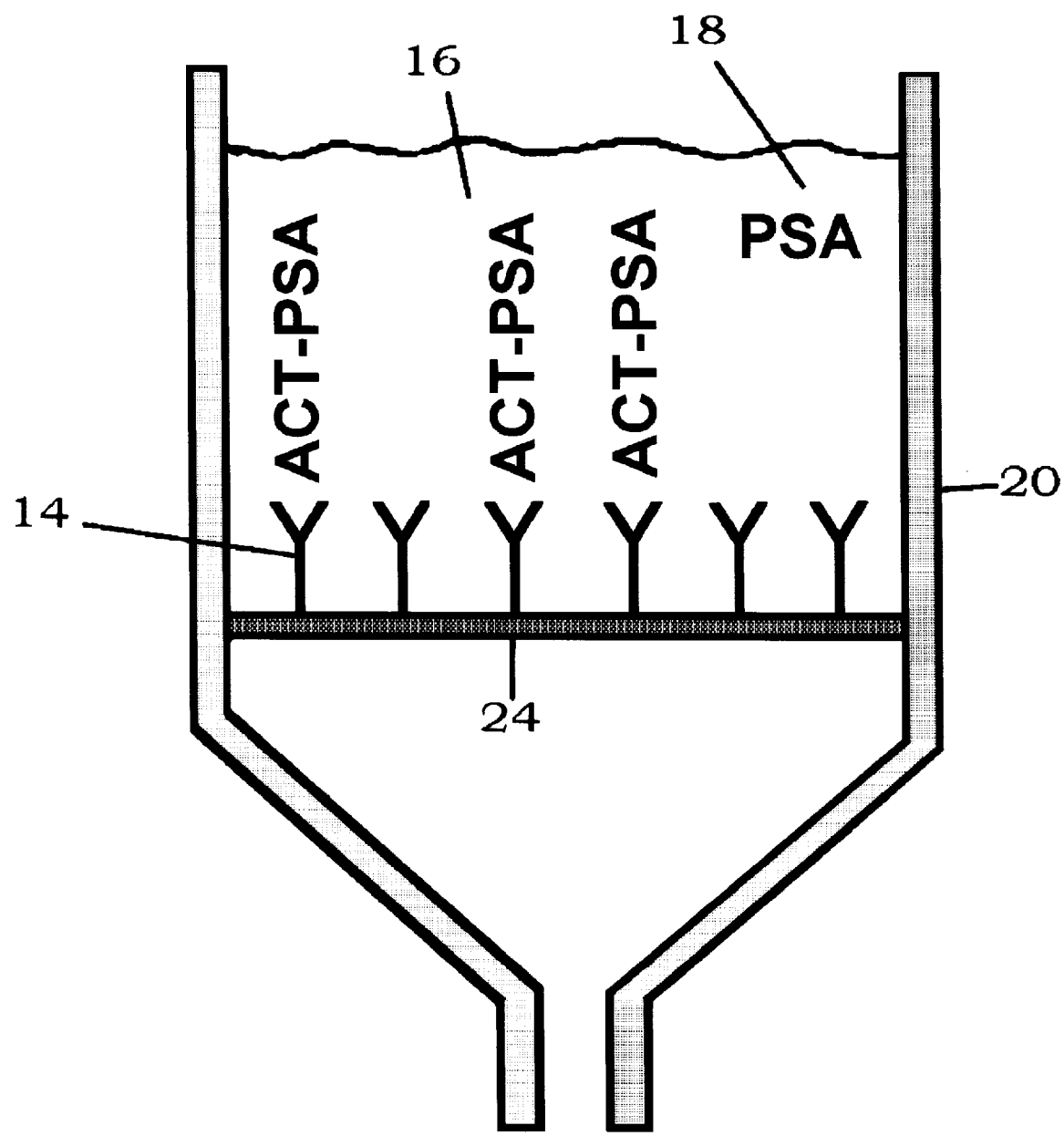
FIG. 2 is a sectional view of a pretreatment filter device in accordance with the present invention.

As shown in FIG. 2, a pretreatment filter device comprises a vessel (20) into which the fluid sample can be placed either by pouring, pipetting, or other conventional means for transferring fluids. One wall or surface of the vessel has an opening (22) for allowing the fluid sample to be removed from the pretreatment device by flowing or being pulled by vacuum downward through the opening. Disposed within and about the opening is a filter media (24) such as cellulose. Attached to the surface of the filter media are an excess of a plurality of antibodies (14) which are specific in binding complexed PSA (16) but not free PSA (18). Suitable antibodies include goat anti-ACT, which are available from Scantibodies Laboratories, Inc. of Santee, Calif. These antibodies can be bound by conventional techniques known to those of skill in the art. The filter media may be a bibulous material capable of drawing fluid sample into the media by capillary action. The volume of bibulous material present is sufficient to attach the excess of antibodies. Suitable bibulous materials include blotting papers, filter papers, non-woven natural polymers, and non-woven synthetic polymers. The dimensions of the materials will vary depending upon sample size and absorptive capacity, as known to the art.

Removable Pretreatment Device

Figure 3:
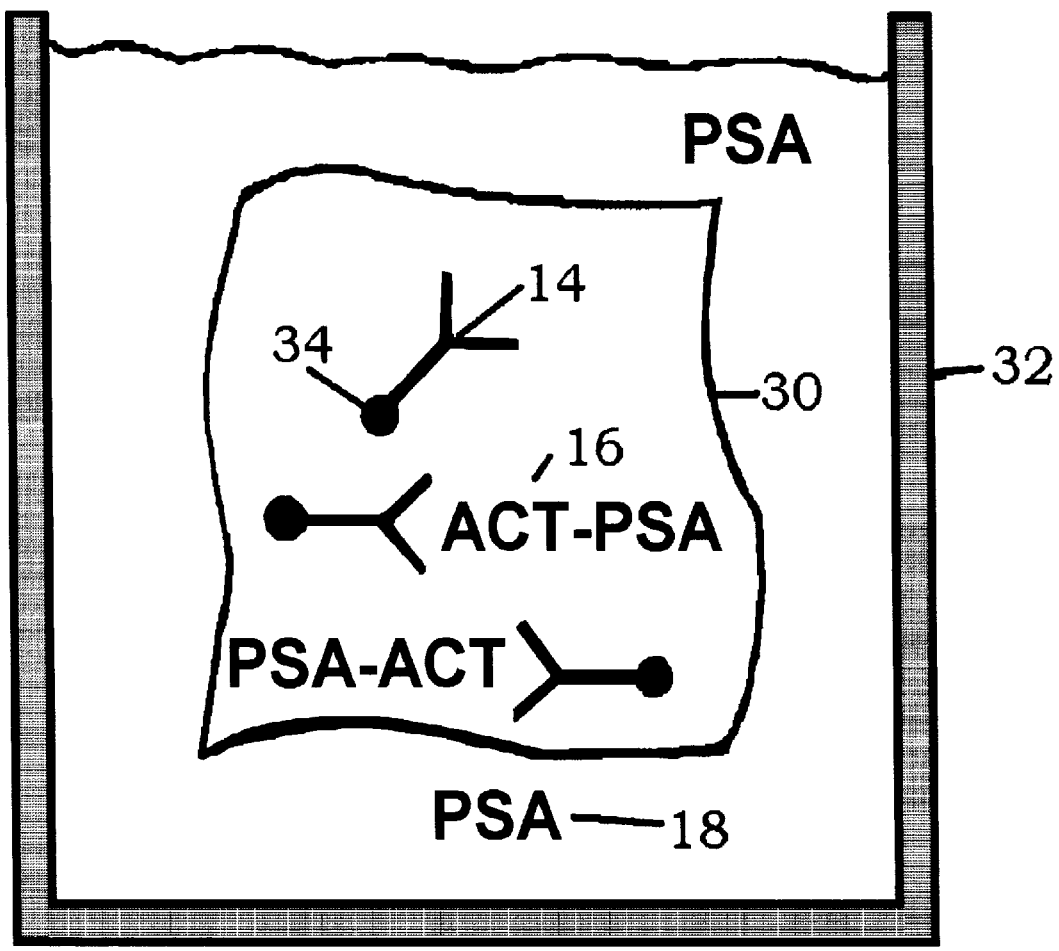
FIG. 3 is a sectional view of a removable pretreatment device in accordance with the present invention.

As shown in FIG. 3, a removable pretreatment device can take the form of a disposable bead pack (30) which may be placed into a container or vessel (32) either before or after placing a fluid sample into the vessel. The pack contains a plurality of beads (34) such as are used in existing immunoassay devices. Suitable bead materials include polystyrene or latex. Attached to the surface of the beads are an excess of antibodies (14) specific to the anti-chymotrypsin portion of complexed PSA. Suitable antibodies include goat anti-ACT, which are available from Scantibodies Laboratories, Inc. of Santee, Calif. These antibodies can be bound by conventional techniques known to those of skill in the art. The pretreatment device is placed into the sample for a time and under condition sufficient to allow any complexed PSA present to bind to the antibodies (14). Only free PSA (18) remains unbound in the fluid sample. The pack may either be withdrawn from the fluid sample and thrown away or the sample may be removed leaving the pack in the vessel. Alternatively, a pretreatment device can be in the form of a coated dipstick or a disposable piece of coated media such as cellulose, nitrocellulose, glass fibers, and the like.

Coated Tube Pretreatment Device

Figure 4:
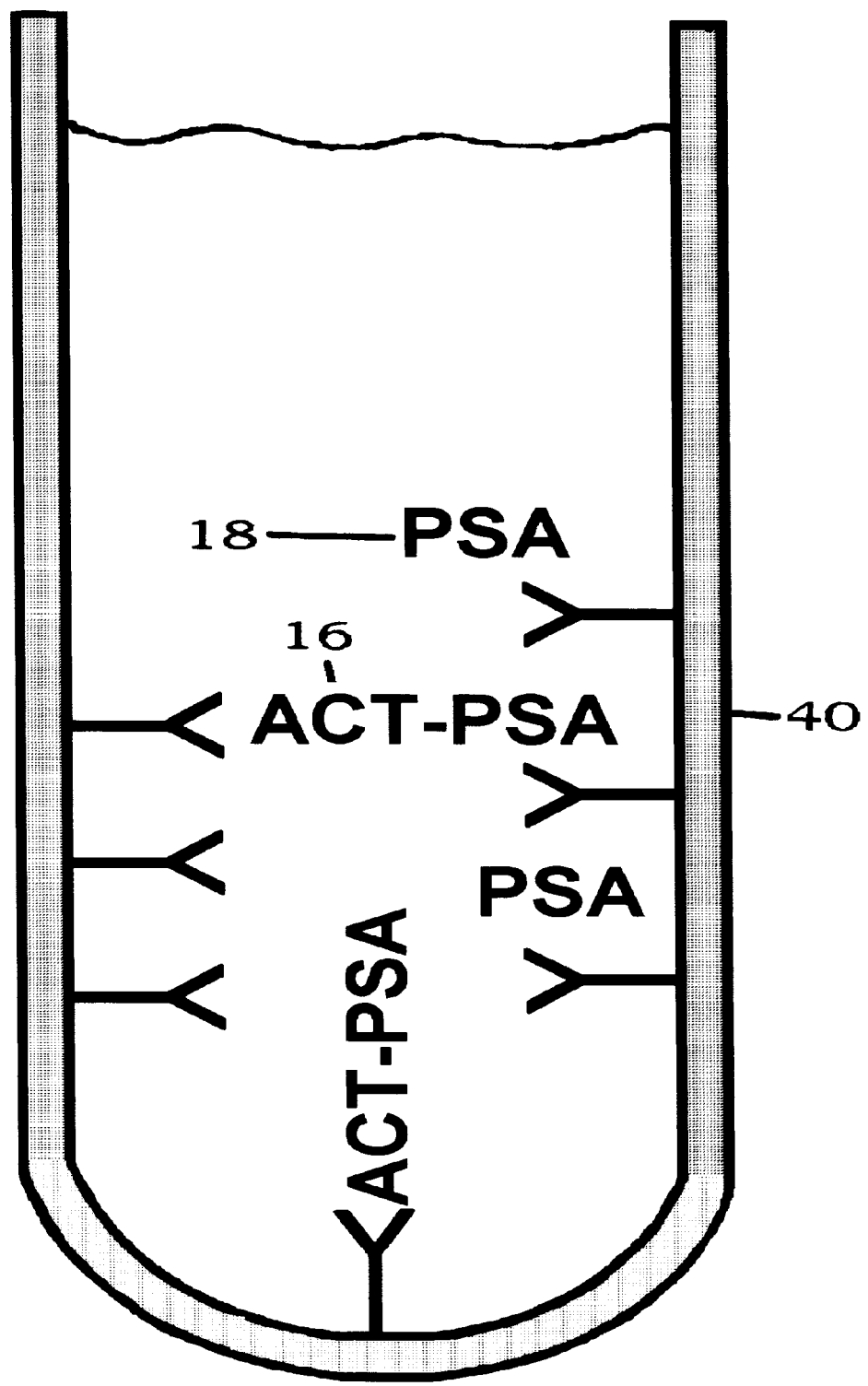
FIG. 4 is a sectional view of a coated tube pretreatment device in accordance with the present invention.

As shown in FIG. 4, a coated tube pretreatment device comprises a vessel (40) having disposed on the interior surfaces (42) an excess of complexed PSA-specific antibodies (14). Suitable antibodies include goat anti-ACT, which are available from Scantibodies Laboratories, Inc. of Santee, Calif. These antibodies can be bound by conventional techniques known to those of skill in the art. In use, complexed PSA (16) will bind to the antibodies, leaving free PSA (18) in the solution.

The ordinarily skilled artisan can appreciate that the present invention can incorporate any number of the preferred features described above.

All publications or unpublished patent applications mentioned herein are hereby incorporated by reference thereto.

Other embodiments of the present invention are not presented here which are obvious to those of ordinary skill in the art, now or during the term of any patent issuing from this patent specification, and thus, are within the spirit and scope of the present invention.

I claim:

1. A method for detecting free prostate specific antigen (PSA) in a biological sample using an assay that incorporates a specific binding reaction comprising:

a) contacting a biological fluid sample containing a mixture of complexed PSA and free PSA with a pretreatment device, said pretreatment device having attached thereto an excess of at least one specific binding partner which specifically binds only to complexed PSA and not to free PSA, leaving any free PSA unbound;

b) keeping the fluid sample in contact with the pretreatment device for a time sufficient to bind all complexed PSA to the attached at least one specific binding partner;

c) removing the fluid sample from the device;

d) exposing the fluid sample to the specific binding assay reagents for detecting free PSA under conditions which permit a measurement of free PSA; and e) measuring the amount of free PSA present in the sample.

2. The method of claim 1 wherein the fluid sample is removed from the pretreatment device by flowing or being pulled by vacuum downward through the pretreatment device.

3. The method of claim 1 wherein the fluid sample is placed into a container prior to contact with the pretreatment device and the pretreatment device is placed into and withdrawn from the fluid sample.

4. The method of claim 1 wherein the fluid sample is placed into a container prior to contact with the pretreatment device, the pretreatment device is placed into the fluid sample, and the fluid sample is withdrawn from the container.

5. The method of claim 1 wherein the at least one specific binding partner is an antibody specific for the α1-antichymotrypsin portion of complexed PSA.

6. A method for detecting free prostate specific antigen (PSA) in a biological sample using an assay that incorporates a specific binding reaction comprising:

a) contacting a biological fluid sample containing a mixture of complexed PSA and free PSA with an excess of at least one first specific binding partner which specifically binds only to complexed PSA and not to free PSA, leaving any free PSA unbound;

b) keeping the fluid sample in contact with the first specific binding partner for a time sufficient to bind all complexed PSA;

c) adding an excess of at least one second specific binding partner which specifically binds to the first binding partner, thereby forming an insoluble complex containing complexed PSA, the first binding partner and the second binding partner;

d) keeping the fluid sample in contact with the second specific binding partner for a time sufficient to bind all complexed PSA which is bound to the first specific binding partner;

e) removing the insoluble complex from fluid sample;

f) exposing the fluid sample to specific binding assay reagents for detecting free PSA under conditions which permit a measurement of free PSA; and g) measuring the amount of free PSA present in the fluid sample.

7. The method of claim 6 wherein the second specific binding partner is an antibody specific for an epitope on the first specific binding partner which is not specific for the α1-antichymotrypsin portion of complexed PSA.

8. The method of claim 6 wherein the first specific binding partner is an antibody specific for the α1-antichymotrypsin portion of complexed PSA.

9. A method for detecting free prostate specific antigen (PSA) in a biological sample using an assay that incorporates a specific binding reaction comprising:

a) contacting a biological fluid sample containing a mixture of complexed PSA and free PSA with an excess of at least one first specific binding partner which specifically binds only to complexed PSA and not to free PSA, leaving any free PSA unbound;

b) keeping the fluid sample in contact with the first specific binding partner for a time sufficient to bind all complexed PSA;

c) adding an excess of at least one second specific binding partner which specifically binds to the first binding partner, thereby forming an insoluble complex containing complexed PSA, the first binding partner and the second binding partner;

d) keeping the fluid sample in contact with the second specific binding partner for a time sufficient to bind all complexed PSA e) exposing the fluid sample to specific binding assay reagents for detecting free PSA under conditions which permit a measurement of free PSA; and f) measuring the amount of free PSA present in the fluid sample.

10. The method of claim 9 wherein the second specific binding partner is an antibody specific for an epitope on the first specific binding partner which is not specific for the α1-antichymotrypsin portion of complexed PSA.

11. The method of claim 9 wherein the first specific binding partner is an antibody specific for the α1-antichymotrypsin portion of complexed PSA.

* * * * *